United States Patent
Dittmer et al.

(10) Patent No.: US 10,212,836 B2
(45) Date of Patent: Feb. 19, 2019

(54) ELECTRICAL BUSHING WITH CONTACT ELEMENT AND METHOD FOR THE PRODUCTION

(71) Applicant: Heraeus Deutschland GmbH & Co. KG, Hanau (DE)

(72) Inventors: Robert Dittmer, Hanau (DE); Frank Krüger, Nidderau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days.

(21) Appl. No.: 15/875,014

(22) Filed: Jan. 19, 2018

(65) Prior Publication Data
US 2018/0213665 A1  Jul. 26, 2018

(30) Foreign Application Priority Data
Jan. 23, 2017  (EP) .................................. 17152617

(51) Int. Cl.
*H05K 5/02* (2006.01)
*H05K 5/00* (2006.01)
(Continued)

(52) U.S. Cl.
CPC ......... *H05K 5/0247* (2013.01); *A61N 1/3754* (2013.01); *C25D 3/48* (2013.01);
(Continued)

(58) Field of Classification Search
CPC .. H05K 5/0247; H05K 5/0095; A61N 1/3754; C25D 7/00; C25D 5/34; C25D 17/12; C25D 3/48
(Continued)

(56) References Cited

U.S. PATENT DOCUMENTS 5,515,604 A * 5/1996 Horine ................... H01R 12/52
29/830
2008/0119906 A1* 5/2008 Starke .................. A61N 1/3754
607/36
(Continued)

FOREIGN PATENT DOCUMENTS

DE  69729719  7/2005
EP  3058984  8/2016

*Primary Examiner* — Sherman Ng
(74) *Attorney, Agent, or Firm* — Dicke, Billig & Czaja, PLLC

(57) ABSTRACT

One aspect relates to an electrical bushing for a medically implantable device, including an electrically insulating base body and an electrical conducting element. The conducting element includes a cermet, and the base body and the conducting element are connected by a sintered bond with a hermetic seal against the base body. The conducting element extends from a first surface of the base body through the base body to a second surface of the base body. The conducting element has first and second electrically conductive areas, and at least one of the electrically conductive areas is at least partially superimposed by a layer-like contact element, including a metal, so that the conducting element is connected in an electroconductive manner via the contact element. The contact element is an electrochemically created layer, such that it has a porous structure, wherein the porosity of the contact element is not more than 20%.

18 Claims, 6 Drawing Sheets

(51) Int. Cl.
    *A61N 1/375*     (2006.01)
    *C25D 17/12*     (2006.01)
    *C25D 3/48*     (2006.01)
    *C25D 5/34*     (2006.01)
    *C25D 7/00*     (2006.01)

(52) U.S. Cl.
    CPC ............... *C25D 5/34* (2013.01); *C25D 7/00* (2013.01); *C25D 17/12* (2013.01); *H05K 5/0095* (2013.01)

(58) Field of Classification Search
    USPC ........................................................ 174/650
    See application file for complete search history.

(56) References Cited

U.S. PATENT DOCUMENTS

| | | | |
|---|---|---|---|
| 2011/0186349 A1* | 8/2011 | Troetzschel | B28B 1/00 174/650 |
| 2011/0190885 A1 | 8/2011 | Troetzschel et al. | |
| 2012/0193118 A1 | 8/2012 | Kempf et al. | |
| 2012/0194981 A1 | 8/2012 | Kempf et al. | |
| 2012/0197326 A1* | 8/2012 | Pavlovic | H01R 43/20 607/5 |
| 2015/0122875 A1* | 5/2015 | Pavlovic | A61N 1/3754 228/121 |

* cited by examiner

ELECTRICAL BUSHING WITH CONTACT ELEMENT AND METHOD FOR THE PRODUCTION

CROSS-REFERENCE TO RELATED APPLICATION

This Utility patent application claims priority to European Patent Application No. EP 17152617.1, filed on Jan. 23, 2017, which is incorporated herein by reference.

BACKGROUND

DE 697 297 19 T2 describes an electrical bushing for an active, implantable, medical device—also identified as implantable device or therapy device. Such electrical bushings serve the purpose of establishing an electrical connection between a hermetically sealed interior and an exterior of the therapy device. Known implantable therapy devices are pacemakers or defibrillators, which typically have a hermetically sealed metal housing, which is provided with a connection body, also called header or head part, on one side. The connection body serves for the connection with electrode leads. The connection socket has electrical contacts for electrically connecting the electrode leads to the control electronics in the interior of the housing of the implantable therapy device. On the one hand, provision is thereby made for electrical connections between the connection body and the outer side of the electrical bushing. On the other hand, provision is made for electrical connections between the inner side of the bushing and the control electronics.

The hermetic seal with regard to a surrounding area is a significant prerequisite for an electrical bushing. Conducting elements, which are introduced into an electrically insulating base body and via which the electrical signals proceed, need to thus be introduced into the insulating base body without any gaps. It has proven to be advantageous thereby to embody the conducting elements as cermet. Cermets are composite materials of powdery metal and one or a plurality of ceramics. Cermets make it possible to produce a direct substance-to-substance bond between the conducting element and the surrounding insulating ceramic base body of the bushing by means of co-sintering. If massive metallic conducting wires are used instead of cermets, they need to be introduced into the ceramic in extensive methods in order to establish a hermetically sealed connection. Methods, which require a metallization of the ceramic in the through opening and soldering processing by using solder rings, are used thereby. In particular the metallization in the through opening has proven to be difficult to apply.

On the other hand, cermet composite materials have a limited metal content. In many cases, direct sufficiently stable connections can thus not be established with the help of metal wires between the exposed surfaces of a cermet conducting element and the connection body on the outer side or the control electronics, respectively, on the inner side of a housing. The wires, which are used, often only have a diameter of a few micrometers. Depending on the particle size of the metal or ceramic powder, respectively, which is used, the metal particles in the cermet surface of the exposed area of the conducting element have such a large distance from one another that a reliable direct contacting with a metal wire is not possible in many cases. In such cases, a connection layer, also contact element, which ensures a sufficiently high-tensile connection between the cermet conducting element and a metal wire, is thus required. The contact element is arranged between the conducting element of the electrical bushing and the metal wire. The contact element typically consists of a suitable metal or of a suitable metal alloy.

Such contact elements can be created with known methods, such as printing or PVD methods.

Known printing methods are pad printing and screen printing. If the connection layer is applied via a printing method, a printing paste can be used for example, which includes at least one conducting material. In addition, the paste oftentimes also includes one or a plurality of organic binding agents, such as, for example, an alkyl cellulose. When removing the binding agent by means of heating, a metal layer is obtained, which, on principle, has a strong porosity.

The sputtering, which is known as cathode sputtering process, is a known PVD method. By bombarding with high-energy ions, atoms, which subsequently settle on the substrate, in this case the conducting element, as layer, are knocked out of a solid. Layers created in this way often have a low porosity. The creation of PVD-generated layers with large layer thicknesses is economically unviable.

Printing methods as well as PVD methods are mask-giving methods. If only certain areas of a substrate, here the exposed surfaces of the conducting element, are to be coated with the contact element, a masking of the surrounding areas is required. Masking methods frequently reach their limits at those locations, where very small surfaces or surfaces, which are located closely next to one another, are to be coated. Due to the advancing miniaturization and devices, which become increasingly more complex, this is often associated with problems in the medical technology. Moreover, the printing methods cannot be used to coat curved surfaces. As mentioned above, printing methods often lead to highly-porous connection layers or contact elements, which do not provide for a high-tensile connection with a metal wire. If larger layer thicknesses are required for the contact element, PVD methods are economically not viable. In general, mask-giving methods are not suitable in the case of surfaces to be coated, which are very small and/or which are located closely next to one another.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
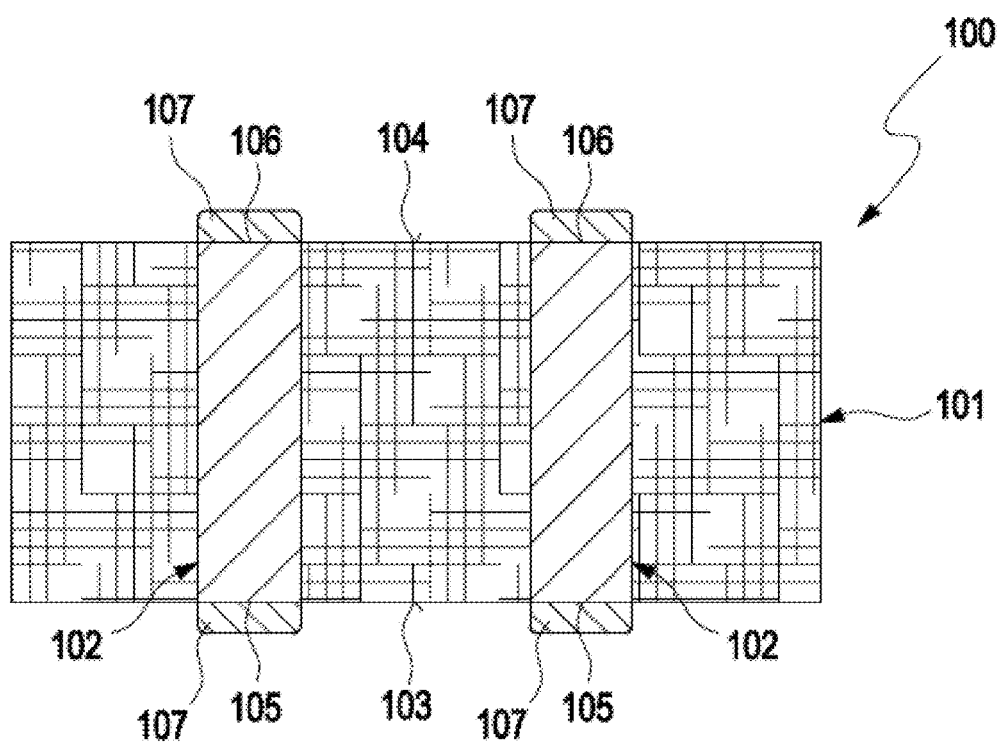
FIG. 1 illustrates a cross sectional illustration of a bushing according to one embodiment.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

In general, it is an object of the embodiments at hand to at least partially overcome the above-mentioned disadvantages of the prior art. The object of one embodiment is to be seen in providing an electrical bushing including a contact element, which superimposes the exposed surface of a cermet conducting element, wherein the contact element is embodied in such a way that it can be created across a small surface, that it covers the exposed surface of the conducting element without a border, if possible, and that is has such a low porosity that a high-tensile connection with a metal wire or another metal-containing wire-like structure can be created. It is a further object of one embodiment to provide a method, which makes it possible to establish electrical bushings with contact elements, which fulfils the above-mentioned criteria. One method is to make it possible to provide bushings with contact elements on curved surfaces. The method needs to simultaneously make it possible to create contact elements on conducting elements, which are located closely next to one another, without the contact elements touching one another.

The independent claims make a contribution to at least partially fulfilling at least one of the above objects. The dependent claims provide additional embodiments, which contribute to at least partially fulfilling at least one of the objects. The expressions "having", "comprising" or "including" etc. do not rule out those further elements, ingredients etc. can be included. The indefinite article "a" does not rule out that a plurality can be present.

In a first aspect of one embodiment, an electrical bushing for a medically implantable device is proposed, including an electrically insulating base body and an electrical conducting element, wherein the conducting element includes a cermet, and wherein the base body and the conducting element are connected by means of a substance-to-substance sintered bond, so that the conducing element is hermetically sealed against the base body; the conducting element extends from a first surface of the base body through the base body to a second surface of the base body, wherein the conducting element has a first electrically conductive area within the first surface of the base body and a second electrically conductive area within the second surface of the base body, and at least one of the electrically conductive areas is at least partially superimposed by a layer-like contact element, which includes a metal, so that the conducting element can be connected in an electroconductive manner via the contact element, wherein the contact element is an electrochemically created layer, and the contact element has a porous structure, wherein the porosity of the contact element is not more than 20%.

Due to the fact that the contact element is an electrochemically created layer, a mask-giving method is not required. The electrochemical deposition for creating the layer only takes place in an area, in which electrically conductive particles are in fact present. In the case of the electrochemical deposition, this is only the case at the exposed surfaces of the conducting element, that is, on the electrically conductive area within the insulating base body. Surprisingly, it was determined thereby that a contact element can be created, which is sufficiently sealed and which is located on the conducting element in a sufficiently firmly adhering manner, in spite of the mixture of metal particles and the ceramic particles caused by the cermet, and the spatial separation of these particles within the bond. The contact element thereby has a porosity of not more than 20% and is thus suitable for attaching metal wires. Bonds with a sufficient tensile strength are thus obtained. Welding methods, such as, for example, resistance welding, ultrasonic welding, laser welding or a microprocess welding method, are suitable to attach the metal wires to the contact element.

In the case of the microprocess welding method, for example a pressure, which is limited in time, acts on the interface of wire to the contact element for several minutes to hours. Moreover or in the alternative, work can be performed at an increased temperature, in one embodiment in the range of 180-220° C. Furthermore or in the alternative, the microprocess welding method can be carried out under the impact of ultrasonic waves. Wedge-shaped or spherical substance-to-substance bonds, respectively, can be attained by means of the materials of the wires and of the contact element, which are treated in this way. In one embodiment, wires with a round cross section are used.

Wire bonding methods, such as ball-wedge bonding or wedge-wedge bonding, which are known from the construction and joining technology, are also suitable.

Due to the fact that the contact element is an electrochemically created layer, the layer-like contact element is virtually congruent with the coated surface of the contact element. The layer-like contact element thus covers the conductive surface of the conducting element without a border or virtually without a border. A growth of the layer in the radial or the lateral direction is to be expected only in the case of larger layer thicknesses.

The contact element is an electrochemically created layer, which is obtained by means of electrochemical deposition. "Electrochemical deposition" refers to all methods, which lead to a deposition of a metal from an electrolytic bath on a metal-containing conductive surface. In response to the deposition on this conductive surface, metal cations are reduced to the elemental metal. The area to be coated represents the cathode. Typically, the deposition takes place in a purely aqueous environment, whereby the metal cations and counterions (anions) are present so as to be dissolved in water. However, it does not need to be a purely aqueous environment. In certain cases, the presence of organic solvents can be advantageous. An electrical current can thereby be applied from the outside. However, currentless methods are also conceivable, in the case of which the deposition runs spontaneously by selecting a suitable redox system, without having to apply an electrical current from the outside. For example, reduction methods are used in these cases, in which a reducing agent is added to the electrolyte. The oxidation of the reducing agent by adding electrons thereby leads to a reduction of the metal cations. To provide for a specific deposition from such solutions, the metal deposition with a reducing agent must only run under the catalytic influence of the surface of the contact element, which is to be coated, because an unspecific deposition of all surfaces would otherwise take place. Palladium-containing solutions, which seed the surface of the conducting element, so that this surface subsequently becomes catalytically active in a nickel bath, for example, can be used for the activation.

The porosity of the electroconductive contact element represents the ratio of void volume of the contact element to the total volume of the contact element. For example, a contact element with a total volume of 1 mm$^3$ and a void volume of 0.15 mm$^3$ has a porosity of 15%. The contact element in one embodiment has a porosity of at least 0.1%. The specification of the percentage of the porosity is specification in percent by volume (vol. %).

On the one hand, the electroconductive contact element has the characteriztic of establishing a firm and mechanically durable connection to the conducting element, on the other hand, of establishing a simple, yet mechanically durable connection to further electroconductive elements, which are to be connected to the conducting element. Due to the fact that the conducting element is made at least partially of a cermet and for example has ceramic components in part, a connection to further electroconductive materials, as described above, is not readily possible. It is thus advantageous to add a contact element, which provides for a connection, which can be established easily and which is firm, to the conducting element on the one hand and for example with the wire on the other hand, from the electrical bushing to electroconductive materials, such as, for example, a wire, which is to be connected to the conducting element.

As a rule, the electroconductive contact element connects to a wire-like structure. In one embodiment, the contact element is connected via the wire-like structure to one or a plurality of elements of the electronic unit of an implantable device. A wire-like structure can be understood to be a wire or an embossed wire structure. The wire-like structure is able to conduct electrical current. A resistance in a range of 0.1 to 0.5 Ohm mm$^2$/m should not be exceeded thereby. The wire-like structure should furthermore provide for a connection between the conducting element of the electrical bushing and a further electrical device, such as, for example, a further cermet, a battery or another electrical unit.

A composite material of one or a plurality of ceramic materials in at least one metallic matrix or a composite material of one or a plurality of metallic materials in at least one ceramic matrix or both is identified as "cermet". A mixture of at least one ceramic powder and at least one metallic powder, for example, can be used to produce a cermet. At least one binding agent and optionally at least one solvent can be added to this mixture, to obtain a pliable green body. In response to the so-called debinding, the binding agent and, if applicable, the solvent are later removed completely either thermally or by vaporization, respectively.

As a rule, an electrically conductive connection appears in the cermet, when the metal content lies above the so-called percolation threshold, at which the metal particles in the sintered cermet are at least selectively connected to one another, so that an electrical conduction is made possible. According to experience, the metal content needs to be at least 25% by volume, depending on the material selection.

The ceramic component of the cermet is in one embodiment selected from the group consisting of an oxide ceramic, a silicate ceramic, a non-oxide ceramic and an element ceramic or a mixture of at least two of them.

The oxide ceramic is in one embodiment selected from the group consisting of a metal oxide, a semi-metal oxide or of a mixture thereof. The metal of the metal oxide can be selected from the group consisting of aluminium, beryllium, barium, calcium, magnesium, sodium, potassium, iron, zirconium, titanium or a mixture of least two of them. The metal oxide is in one embodiment selected from the group consisting of aluminium oxide ($Al_2O_3$), magnesium oxide (MgO), zirconium oxide ($ZrO_2$), yttrium oxide ($Y_2O_3$), aluminium titanate ($Al_2TiO_5$), a piezoceramic, such as lead-zirconate ($PbZrO_3$), lead-titanate ($PbTiO_3$) as well as lead-zirconate-titanate (PZT) or a mixture of at least two of them. The semi-metal of the semi-metal oxide is in one embodiment selected from the group consisting of boron, silicon, arsenic, tellurium or a mixture of at least two of them. A further oxide ceramic contains one selected from the group consisting of zirconium oxide-reinforced aluminium oxide (ZTA—zirconium oxide toughened alumina—$Al_2O_3/ZrO_2$), yttrium-stabilized zirconium oxide (Y-TZP), barium (Zr, Ti)oxide, barium(Ce, Ti)oxide or a combination of at least two of them.

The non-oxide ceramic can be selected from the group consisting of a carbide, a nitride or a mixture thereof. The carbide can be selected from the group consisting of silicon carbide (SiC), boron carbide ($B_4C$), titanium carbide (TiC), tungsten carbide, cementite ($Fe_3C$). The nitride can be selected from the group consisting of silicon nitride ($Si_3N_4$), aluminium nitride (AlN), titanium nitride (TiN), silicon aluminium oxynitride (SIALON) or a mixture of at least two of them. A further non-oxide ceramic is sodium-potassium niobate.

The element ceramic is in one embodiment carbon, and in one embodiment diamond. To produce a cermet, which includes an element ceramic as ceramic component, a diamond powder is in one embodiment mixed with a metal powder. Such a cermet with an element ceramic as ceramic component is characterized by a combination of high hardness and high specific heat conductivity.

All metals known to the person of skill in the art, which have a good tolerability with eukaryotic tissue, are possible for metallic components of the cermet. In one embodiment metal is selected from the group consisting of platinum, iridium, niobium, palladium, iron, stainless steel, cobalt-chromium alloy, molybdenum, tantalum, tungsten, titanium, cobalt and zirconium or a combination of at least two of them. In one embodiment combination is thereby an alloy. In one embodiment stainless steel is a stainless steel 316L. In one embodiment metal is bio-compatible. In one embodiment alloy is bio-compatible. In one embodiment bio-compatible metal is one selected from the group consisting of palladium, rhodium, ruthenium, molybdenum, platinum, iridium, tungsten, gold, titanium, niobium and tantalum or a combination of at least two of them.

The base body and the at least one conduction element are connected to one another by means of a substance-to-substance sintered bond. Substance-to-substance means that the two parts, which are to be connected, form a unit after the connection and that the connection itself has a strength, which corresponds at least to a strength of the two parts. This can have the result that the connected parts do not break apart at the connection point in response to mechanical or pressure load, but at a different location of the two connected parts. It can be ensured through this that the connection is just as or not as porous or gas-permeable or moisture-permeable as the parts themselves, which are to be connected.

In the context of one embodiment, a sintering, a sintering process or a co-sintering is generally understood as a method for producing materials or workpieces, in response to which powdery substances, in particular one selected from the group consisting of fine-grained substances, ceramic substances and metallic substances, or a combination of at least two of them, are heated and thus connected. This process can take place without external pressure onto the substance to be heated, or can take place at an increased pressure on the substance to be heated, for example at a pressure of at least 2 bar, in one embodiment higher pressures, for example pressures of at least 10 bar, at least 100 bar or even at least 1000 bar. The process can in particular take place completely or partially at temperatures of below the melting temperature of the powdery materials, for example at temperatures of 700° to 1400° C. The process can be carried out completely or partially in a tool or in a mold or in both, so that a shaping can be associated with the sintering process. In addition to the powdery materials, a starting material for the sintering process can include further materials, for example one or a plurality of binding agents or one or a plurality of solvents or both. The sintering process can take place in one step or also in a plurality of steps, whereby further steps can for example precede the sintering process, for example one or a plurality of shaping steps or one or a plurality of debinding steps or both. The sintering or the sintering process, respectively, thus corresponds to a firing process. The sintering process, for a cermet, can run similarly to a sintering process, which is typically used for homogeneous powder. For example, the material can be compressed in response to the sintering process at a high temperature and, if applicable, high pressure, so that the cermet is virtually sealed, or has a maximally sealed porosity. As a rule, cermets are characterized by a particularly high hardness and wear-resistance.

In one embodiment the electrical bushing is characterized in that the contact element completely superimposes the conductive area.

An embodiment of the electrical bushing, which is characterized in that the amount of the surface of the layer-like contact element is not more than 25% larger than the amount of the surface of the superimposed conductive area, in one embodiment not more than 10% larger, in one embodiment not more than 5% larger. In one embodiment, both surfaces are substantially congruent or congruent to one another. In one embodiment, the amount of the surface of the contact element is not more than 1% larger than the amount of the surface of the superimposed conductive area of the conducting element.

The surface of the electrically conductive contact element is understood to be that surface, which results from the projection of that surface, which can be seen in the case of a perpendicular top view onto the electrical bushing. In the ideal case, the surface of the contact element corresponds to the surface of the electrically conductive area of the conducting element within the surface of the base body, and both surfaces are completely congruent. In this case, the contact element would cover the conductive area of the conducting element within the surface of the base body completely without a border. As already specified above, a growth of the layer-like contact element in the radial or lateral direction starts as the electrochemical deposition proceeds. As a rule, the amount of the surface of the contact element is thus slightly larger than the surface of the conductive area of the conducting element. It can nonetheless be assumed that both surfaces are largely congruent, thus approximately congruent, as a result of the electrochemical separation.

This has a number of advantages. When using noble metal for the contact element, valuable material is saved due to the congruence, because only those surfaces are coated, which are in fact needed for contacting with a metal wire.

Due to the congruence, a subsequent, automated joining process for attaching a metal wire to the contact element is also facilitated. If the contact element is significantly larger with regard to the amount of its surface than the electrically conductive area of the conducting element, an optical detection could not identify accurately, where exactly the conducting element is located below the contact element. If the contact element is significantly smaller with regard to the amount of its surface than the electroconductive area of the conducting element, the attaching of the wire to the contact element would be difficult, in particular in the case of conducting elements with small diameters. Only very fine wires could then be used. It is thus important in this case to utilize the entire surface, which is provided by the conducting element. Wires with larger diameters can thus be used and the resistance of the system can be minimized. This applies, for example, to the transition resistance from the cermet conducting element to the contact element.

One embodiment of the electrical bushing is characterized in that the cermet has a metal portion of at least 25% by volume, in one embodiment includes a metal portion of 30% by volume to 90% by volume, in one embodiment includes a metal portion of 35% by volume to 60% by volume, and in one embodiment includes a metal portion of 40% by volume to 50% by volume.

The percent by volume of the metal is defined as the quotient of the percent by volume of the metal particles by the sum from the percent by volume of the metal particles and the percent by volume of the ceramic particles.

The cermet must have a minimum amount of metal particles, so that the percolation threshold is reached and exceeded. Surprisingly, it has been determined that a metal portion of 25% by volume is sufficient to obtain a low-porous and thus a sealed and firmly adhering contact element. In spite of the low content of metal particles, a sufficiently high number of germ spots appear to be present on the surface, so that a correspondingly sealed and firmly adhering contact element is obtained in response to the electrochemical deposition. A sufficient hermeticity of the connection between the conducting element and the base body is no longer inevitably ensured above a metal content of 90% by volume, because the substance-to-substance bond between the conducting element and the base body is reached by sintering together or co-sintering the ceramic particles in the cermet and in the base body.

One embodiment of the electrical bushing is characterized in that the contact element has an average layer thickness of between 1 μm and 50 μm, in one embodiment an average layer thickness of between 5 μm and 35 μm, in one embodiment an average layer thickness of between 10 μm and 20 μm, and in one further embodiment a layer thickness of 15 μm.

To establish high-tensile connections between a metal wire and the contact element, the mentioned layer thicknesses are preferred. A layer thickness of 1 μm is to not be fallen below thereby, so that the layer-like contact element does not melt completely in some areas, for example in response to the laser welding. As a result, a direct connection is created in some areas between the metal wire and the cermet conducting element, which, in certain cases, does not have a sufficient tensile strength. Layer thicknesses, which are too large, result in long coating times and can thus become impracticable and uneconomical.

One embodiment of the electrical bushing is characterized in that the porous structure of the contact element has a sealed porosity at at least 70% by volume, has a sealed porosity in one embodiment at at least 90% by volume, and in one embodiment has a completely sealed porosity. The information in % by volume provided in this context represents the portion of the volume of the entire pore volume.

Due to the parameters, which are used in response to the electrochemical deposition, such as, for example, the current density and the concentration of the electrolyte, it can be adjusted, whether the contact element has a sealed or open porosity or mixed forms thereof after the deposition. Sealed porosity means that the pores are not in connection with one another. Open porosity means that the pores are connected among one another. It has been determined that a sealed porous form leads to mechanically more stable connections between the wire-like structure and the contact element.

One embodiment of the electrical bushing is thereby characterized in that the contact element has a porosity of 0.1 to 10% by volume, in one embodiment of 0.2 to 2% by volume, and in one embodiment of 0.2 to 0.5% by volume.

Layers of the contact element created by means of electrochemical deposition adhere particularly well to the superimposed cermet conducting element, when the porosity of the contact element lies within one of the ranges, which has been mentioned as being preferred.

One embodiment of the electrical bushing is characterized in that the contact element has a porosity gradient.

By means of a corresponding selection of the parameters in response to the electrochemical deposition, the electrochemically created layer of the contact element can be provided with a porosity gradient. This can be done easily in particular by means of a variation of the current intensity in response to the galvanic coating. In the case of low current densities, contact elements with a lower porosity are thus obtained. In the case of high current densities, contact elements with higher porosity are obtained. The porosity thus tends to increase with the current density applied in response to the deposition.

One embodiment of the electrical bushing is thereby characterized in that the average porosity of the area adjacent to the conducting element is lowest and that the average porosity increases as the distance from the area adjacent the conducting element increases.

One embodiment of the electrical bushing is thereby characterized in that the averaged roughness depth Rz of the layer-like contact element is between 0.2 μm and 20 μm, in one embodiment between 0.5 μm and 12 μm, and in one embodiment between 1 μm and 6 μm.

Small roughness depths, that is, a high quality of the surface quality, lead to higher tensile strengths of a metal wire, which is welded to a contact element. Surprisingly, it has been determined that low roughness depths in response to the electrochemical coating are obtained when the substrate (base body and electrically conductive area of the conducting element within the base body) is pre-treated by smooth grinding and polishing.

One embodiment of the electrical bushing is characterized in that the metal powder used for the cermet of the conducting element has an average particle size of 0.5 μm to 5 μm, in one embodiment an average particle size of 0.5 μm to 3 μm, in one embodiment an average particle size of 0.7 μm to 2 μm and in one further embodiment an average particle size of 0.9 μm to 1.9 μm.

"Average particle size" is thereby understood as the $d_{50}$ value of the particle size distribution, also 50% quantile or median value. Metal particles with a smaller average particle size provide for a large number of germ locations in response to the electrochemical coating, so that firmly adhering and sealed layers with low porosity are obtained under these conditions. Further, in one embodiment, the width of the particle size distribution is not to be too large, that is particles, which are too large, must not be present in the metal powder fraction. The selected fraction of the metal powder in one embodiment has a width of a total of not more than 10 μm, in one embodiment of not more than 8 μm and in one embodiment of not more than 5 μm.

One embodiment of the electrical bushing is thereby characterized in that the ceramic powder used of the cermet has an average particle size of 0.1 μm to 10 μm, in one embodiment of 0.5 μm to 4 μm, in one embodiment of 1 μm to 2.5 μm and in one further embodiment of 1.1 μm to 1.8 μm.

The ceramic powder used for the cermet of the conducting element must also not have particles, which are too large, in the selected ceramic particle fraction. If particles, which are too large, are present in the ceramic powder, the average distances between the metal particles become too large. Even if a sufficient number of germ locations are formed on the metal in this case, the growing layer has a porosity, which is at least partially too large, due to the large average distances, between the metal particles, or at least an unfavorable porosity distribution. Further, in one embodiment, the width of the particle size distribution of the ceramic powder is not to be too large, that is particles, which are too large, must not be present in the ceramic powder faction. The selected fraction of the ceramic powder in one embodiment has a width of a total of not more than 20 μm, in one embodiment of not more than 15 μm, and in one embodiment of not more than 10 μm.

One embodiment of the electrical bushing is characterized in that the conducting element includes at least one metal selected from the group consisting of platinum, iridium, niobium, molybdenum, tantalum, tungsten, titanium, cobalt, chromium and zirconium, or that the conducting element includes an alloy of at least two of the above-mentioned metals.

One embodiment of the electrical bushing is characterized in that the contact element includes at least one metal selected from the group consisting of gold, silver, palladium, platinum, copper, chromium, nickel and iron, or an alloy of at least two of the above-mentioned metals.

The contact element can be made of every material, which is known to the person of skill in the art, in order to establish an electrically conductive connection between two bodies. This is why the contact element is in one embodiment made of a metal. Metals, mixtures or alloys, which are at least partially selected from the group consisting of gold, silver, palladium, platinum, copper, chromium, nickel and iron, are in one embodiment thereby.

The metals selected for the cermet of the conducing element and the connecting layer, mixtures thereof and alloys are in one embodiment bio-compatible, which is why they are well suited for use in implantable devices. In one embodiment, bio-compatible metal is selected from the group consisting of bio-tolerant, bio-inert and bio-active or a combination of at least two of them. Bio-compatibility can for example be determined with the standard ISO 10933-4: 2002.

Considerations for the bio-compatibility in one embodiment of the electrical bushing also apply for the ceramic components of the cermet, of the base body, and, if applicable, further components of the electrical bushing.

One embodiment of the electrical bushing is characterized in that the electrically insulating base body has a ceramic.

The base body can be made in particular completely or partially of one or a plurality of sinterable materials, in particular of one or a plurality of sinterable ceramic-based materials.

One embodiment of the electrical bushing is characterized in that the electrically insulating base body includes at least one ceramic selected from the group of aluminium oxide ($Al_2O_3$), zirconium dioxide ($ZrO_2$), aluminium oxide toughened zirconium oxide (ZTA), zirconium toughened aluminium oxide (ZTA-$Al_2O_3$/$ZrO_2$), yttrium-stabilized zirconium oxide (Y-TZP), aluminium nitride (AlN), magnesium oxide (MgO), piezoceramic, barium(Zr, Ti)oxide barium (CE, Ti)oxide or sodium-potassium niobate.

The base body can also be made of one of the above-mentioned ceramics, which are used for the production of the cermet.

One embodiment of the electrical bushing is characterized in that the base body and the cermet have the same ceramic, the base body and the cermet in one embodiment have exclusively the same ceramic, that is, no further ceramic. Aluminum oxide is thereby preferred in one embodiment.

One embodiment of the electrical bushing is characterized in that the electrically insulating base body is formed from a plurality of sintered ceramic layers.

To produce the bushing, a green body film is thereby initially provided and is provided with holes, for example by means of stamping. The holes are filled with a suitable cermet paste. At this stage of the production, the cermet paste includes at least a mixture of metal powder, ceramic powder and an organic vehicle. Pluralities of the green body films, which are filled in this way, are laminated subsequently, so that the cermet-filled holes are arranged on top of one another. They later form the conducting element. So many filled green body films are laminated that the desired thickness of the electrical bushing or length of the conducting element, respectively, is reached. In response to the subsequent firing, the organic vehicle is removed initially; the cermet and the ceramic base body are co-sintered in response to the subsequent transition to higher temperatures. In particular a hermetically sealed substance-to-substance bond is thereby created between the ceramic component of the cermet and the surrounding ceramic of the base body.

One embodiment of the electrical bushing is characterized in that the electrical bushing has a helium leak rate of less than $1*10^{-7}$ atm*$cm^3$/sec. An electrical bushing with such a helium leak rate can be identified as "hermetically sealed".

The term "hermetically sealed" clarifies that moisture and/or gases cannot penetrate or can penetrate only minimally through the hermetically sealed element in response to a use within the typical time periods (for example 5-10 years), as intended. A physical variable, which can for example describe a permeation of gases and/or moisture through a device, for example, through the electrical bushing, is the so-called leak rate, which can be determined for example by means of leak tests. Corresponding leak tests can be carried out for example by means of helium leak testers and are specified in the standard Mil-STD-883G method 1014. The maximally permissible helium leak rate is thereby determined as a function of the internal volume of the device to be tested. According to the methods specified in MIL-STD-883G, method 1014, in paragraph 3.1, and in consideration of the volumes and cavities of the devices to be tested, which appear when using the embodiments at hand, these maximally permissible helium leak rates can for example be from $1 \times 10^{-8}$ atm·$cm^3$/sec, to $1 \times 10^{-7}$ atm·$cm^3$/sec. In the context of one embodiment, the term "hermetically sealed" can mean that the device, which is to be analyzed, for example, the electrical bushing, has a helium leak rate of less than $1 \times 10^{-7}$ atm·$cm^3$/sec. In one embodiment, the helium leak rate can be less than $1 \times 10^{-8}$ atm·$cm^3$/sec, in one embodiment less than $1 \times 10^{-9}$ atm·$cm^3$/sec. For the purpose of standardization, the mentioned helium leak rates can also be converted into the equivalent standard air leak rate. The definition for the equivalent standard air leak rate and the conversion are specified in the standard ISO 3530.

A contribution to fulfilling at least one of the objects according to one embodiment is further made by a method, which includes as method steps:

a) providing an electrical bushing, wherein the bushing
  i. has an electrically insulating base body and an electrical conducting element, wherein the conducting element includes a cermet,
  ii. the base body and the conducting element are connected by means of a substance-to-substance sintered connection, so that the conducting element is hermetically sealed against the base body,
  iii. the conducting element extends from a first surface of the base body through the base body to a second surface of the base body,
  iv. the conducting element has a first electrically conductive area within the first surface of the base body and a second electrically conductive area within the second surface of the base body,
b) applying an electroconductive electrode layer to the first surface of the base body, so that a conductive connection is formed between the first conductive area of the conducting element and the electrode layer,
c) introducing the bushing into a metal-electrolyte solution and forming a metallic contact element in the second electrically conductive area of the conducting element by means of electrochemical deposition by reducing cations of the metal-electrolyte solution,
d) removing the electrode layer.

The electrode layer in step b) serves to establish a reliable electrical connection between the cermet conducting element and the cathode of a direct-current source. This means that the cathode of the direct-current source is connected to the electrical bushing via the electrode layer. It must be ensured thereby that a contacting between the cermet conducting element and the electrode layer is ensured. Due to the fact that the cermet has numerous continuous electrical paths in spite of relatively small metal portions in the compound, an electron excess occurs in the area of the electrode layer as well as on the second electrically conductive area, thus on the exposed surface of the cermet conducting element, when direct current is applied and when the electrode layer is connected as a cathode. Metal cations are thus electrochemically deposited to elemental metal in this area. As a condition for this, the bushing must be immersed as a whole into a metal-electrolyte solution, as long as an electrochemical metal deposition is to take place. An inert electrode, which serves as anode, is simultaneously immersed into the electrolyte solution. The electrode layer is removed again after formation of the metallic contact element, in order to expose the first surface of the base body and the first conductive area of the conducting element or of the conducting elements.

According to step b), a further electrode layer can subsequently optionally be applied to the second surface of the base body, which has already been provided with one or a plurality of contact elements in the area of the second conductive area of the conducting element or of the conducting elements. Steps c) and d) are repeated subsequently, in order to also electrochemically create metallic contact elements in the first conductive area of the conducting element or of the conducting elements.

One embodiment, the method is characterized in that an insulating layer, which superimposes the electrode layer, is applied in a further method step b-1) after step b), so that an electrochemical deposition of a metal does not take place in the area of the electrode layer.

In particular in response to the electrochemical deposition of valuable noble metals, it is undesirable that the deposition of the metal from the electrolyte solution does not only take place in the area of the conducting element, but also on the electrode layer. The electrode layer is at least partially provided with an insulating layer, which superimposes the electrode layer, in this case. In the superimposed areas, a metal deposition can thus not take place at the electrode layer. The insulating layer can consist of every material, which is suitable for the person of skill in the art, for example of a plastic or of a ceramic.

One embodiment, the method is characterized in that the electrical bushing is immersed into an alkaline solution in a further method step b-2) prior to carrying out step c), whereby the electrode layer is connected to a direct-current source and is connected as a cathode, in order to clean the surfaces of the electrical bushing.

In one embodiment, it turned out to be advantageous, when the surfaces of the electrical bushing, in particular the surfaces of the conductive areas of the cermet conducting element, are cleaned prior to the actual electrochemical deposition. For this purpose, the conducting element is connected to the direct-current source, is connected as a cathode, and is immersed into an alkaline solution. A platinised titanium expanded metal can for example serve as anode. When applying direct current, a strong gas development is observed in the area of the cathode, which is caused by the development of molecular hydrogen by reduction of water-bound protons (oxonium ions). The gas bubbles entrain loose particles, adhering fats, oils and other contamination, whereby they are removed from the surface. The alkaline solution furthermore removes thin ceramic films from the cermet surface, whereby these surfaces become more accessible to the electrochemical deposition.

In one embodiment, the method is characterized in that the alkaline solution includes sodium hydroxide and/or potassium hydroxide and optionally includes an addition of a cyanide salt.

The cleaning of the surfaces is particularly effective by using strong alkaline agents, such as sodium or potassium hydroxide. Other strong bases from the group of alkali hydroxides, alkaline earth hydroxides, phosphates, carbonates and sulphides can also be used.

Metallic contaminations can furthermore be removed easily with the help of cyanides, because cyanides have good complexing characteristics, that is, form high complexing constants with many metal ions.

In one embodiment, the method is characterized in that the application of the electrically conductive electrode layer in step b) takes place by pressing an electrically conductive polymer against the second surface.

In many cases, conductive polymers are characterized by a high degree of flexibility. An electrode layer can thus be created by simply pressing a conductive polymer film against the surface of the electrical bushing. A reliable electroconductive connection between the cermet conducting element and the electrode layer is nonetheless created, without having to establish a substance-to-substance bond between the conducting element and the electrode layer. Substance-to-substance bonded electrode layers are more difficult to remove subsequently. Electrode layers applied by means of printing, PVD or cathodes sputtering, for example, require a subsequent mechanical removal.

All polymers, which are known to the person of skill in the art, can be used as conductive polymers. Intrinsically conductive polymers are preferred in one embodiment. Polyaniline, polythiophene, polythieno-thiophene, poly-3,4-ethylenedioxiy-thiophene (PEDOT), polypyrrole and copolymers of the monomers of these polymers and polymers or copolymers from the derivatives of these monomers can be mentioned. Preferably, in one embodiment, poly-3,4-ethylene dioxy-thiophene is used. Depending on the conductivity, the mentioned polymers can also be presented in a doped manner.

In one embodiment, the method is characterized in that the electrode layer is multi-layered, wherein the multi-layer design includes a conductive paste and a conductive film, which superimposes the conductive paste.

Conductive pastes have the advantage that, due to their viscosity, they can be processed in a mechanically simple manner and can be applied well to the surface, so that a complete contacting of the conducting element across the entire exposed surface is attained. A conductive film, which is better suitable than the paste itself for the connection with the direct-current source, can be adhered to the paste in a particularly simple manner. The conductive paste can include an organic vehicle or binding agent, for example an organic polymer or a solvent. After application of the paste, the binding agent is removed, if applicable by heating or by applying a vacuum and an even more firmly adhering electrode layer is thus obtained.

In one embodiment, the electrochemical deposition in step c) takes place by means of galvanizing, whereby the electrode layer is electrically connected to a direct-current source and is connected as a cathode. On principle, galvanic methods have the advantage that the speed of the deposition and the duration can be controlled easily. The speed of the deposition, that is, the increase of the layer thickness per time unit, can be controlled by the current density, that is, by the current intensity per surface unit of the conducting element or of the conducting elements, which are to be coated. The time of the deposition can be controlled easily by turning on and turning off the current flow. Further parameters are the concentration of the electrolyte in the electrolyte solution. The electrolyte solution depletes as the time of the deposition of metal cations progresses. The lowering of the metal-cation concentration is thus in one embodiment preferably compensated by adding an electrolyte solution of a higher concentration, as the deposition time progresses.

In response to the galvanizing, an inert electrode dips into the electrolyte solution next to the electrical bushing, which is connected as a cathode. The inert electrode is thereby electrically connected to a direct-current source and is connected as an anode. The anode is in one embodiment preferably largely or even completely inert. As an example, platinized expanded titanium metal is used. The anode thereby in one embodiment preferably has a much larger surface than the actual substrate, that is, the at least one conductive surface of the cermet conducting element of the electrical bushing. The anodic current density is thus very low. Anode reaction is predominantly the oxidation of water or hydroxide ions to oxygen. Organic compounds, for example grain refiners used in the electrolytes, are also disintegrated anodically in part.

An anode selected from the group consisting of gold electrode, gold-plated copper electrode, platinized titanium electrode and platinized niobium electrode is in one embodiment preferred as inert electrode, whereby platinized titanium electrodes and platinized niobium electrodes are preferred in one embodiment. Depending on the selected system, gold is not completely inert under certain conditions. For example, the gold layer of the anode can dissolve in the electrolytes when using a gold electrolyte to create a contact element of gold. Platinized electrodes are thus preferred in one embodiment in these cases due to the higher standard reduction potential of platinum.

In one embodiment, the method is characterized in that the metal-electrolyte solution includes cations selected from at least one element of the group consisting of gold cations, silver cations, palladium cations, platinum cations, copper cations, chromium cations, nickel cations and iron cations.

Gold cations and platinum cations are further preferred in one embodiment due to the excellent bio-compatibility of these metals. Gold is preferred in one embodiment due to the large number of suitable gold compounds.

In one embodiment, the method is thus characterized in that the metal electrolyte solution includes potassium dicyano aurate (I) and/or potassium tetracyano aurate (III).

In an alternative, the method is characterized in that the electrochemical deposition according to step c) takes place by currentless metal deposition. The deposition thereby runs spontaneously by means of the selection of a suitable redox system, without having to apply an electrical current from the outside.

In one embodiment, the method is characterized in that the current density in response to the electrochemical deposition according to step c), based on the surface of the electrically conductive area, is 0.1 to 100 A/dm$^2$, in one embodiment 0.5 to 30 A/dm$^2$, and in one embodiment 1 to 15 A/dm$^2$.

An electrical bushing for a medically implantable device, which can be obtained by means of one of the embodiments of the above-described method, is furthermore the subject matter of embodiments.

The embodiments of the method are furthermore used to produce an electrical bushing according to one of the above-mentioned embodiments.

Measuring Methods

The following measuring methods were used in the context of embodiments. Unless otherwise specified, the measurements were carried out at an ambient temperature of 25° C., an ambient pressure of 100 kPa (0.986 atm) and a relative humidity of 50%.

Porosity

To measure the porosity, metallographic specimens were initially produced by embedding into epoxy resin, grinding with SiC paper with successively smaller grain size, as well as polishing with a diamond paste. Pictures of the sample surface treated in this way were then taken by means of an optical microscope and an electron microscope. A contrast between the pores of the sample and material (metal and ceramic), which is as high as possible, is to be obtained hereby. To evaluate the images, these greyscale images were converted into binary images by means of the Otsu method. This means that the image pixels were in each case assigned to a pore or to the sample material by means of a threshold value. The porosity was then determined by means of the binary images as quotient from the number of the pixels, which represent pores, and by means of the total number of the pixels per image. The porosity was hereby determined as arithmetic mean from 5 images, in each case recorded at 5 specimens.

Determination of the Layer Thickness of the Contact Element

The layer thickness is determined with the help of a photo-optical measuring microscope from the micrograph of a cross-section polish of a suitable sample as arithmetic mean from 10 measuring points.

Averaged Roughness Depth Rz of the Contact Element

The determination of the averaged roughness depth Rz is made in a contact-free manner with the help of a confocal 3D microscope by the manufacturer Nanofocus (model name: μsurf explorer) according to the standard DIN EN ISO 25178-602.

Exemplary Embodiments

Embodiments will be described in more detail below by means of an exemplary embodiment and drawings, whereby the example and the drawings do not represent a limitation. Unless specified to the contrary, the drawings are not true-to-scale.

Preparation of Ceramic Green Body Films

Ceramic green body films were used as ceramic precursors for the insulating base body. For this purpose, 99.7% by weight of pure $Al_2O_3$ films (Keral 99 by Keramische Folien GmbH) of the thicknesses 400 μm were used. Samples of the green body films were cut to size into 90 mm×90 mm quadrants. Approximately circular holes with a diameter of 400 μm were punched with a mechanical puncher (CPC923101 by Groz-Beckert KG) for 400 μm diameter in an automated punch (MP4150 punch by Unichem Industries Inc.) into the film samples. At least 4 film samples were prepared in this way.

Filling

The holes prepared as above were filled with cermet paste with the help of a stencil by Christian Koenen GmbH and an EKRA Microtronic II printer (model M2H).

For the cermet paste, 60 g of a platinum powder were mixed with 24 g of an $Al_2O_3$ powder with an ethyl cellulose-based organic binding agent and were homogenized with a 3-roller mill. Pastes obtained in this way had viscosities in a range of between 250 to 300 Pa*s (measured with a Haake Rheostress 6000 Rheometer at 25° C.) and a fineness of grind (FoG) of less than 10 μm. The rheology of the pastes was suitable for the subsequent stencil printing.

The thickness of the stencil was 100 µm. The openings of the stencil had the same dimensions and positions as the holes, which were punched into the green body film as described above. The printing parameters were 50 N blade pressure, blade sped forwards 25 mm/s, blade speed backwards 25 mm/s and snap off 0.0 mm. The blade circle was adjusted in such a way that paste material was introduced in response to the forwards movement as well as in response to the backwards movement.

10 minutes after filling of the samples, they were place into a drier HHG-2 (by BTU International Inc.) and were dried therein for 10 minutes at 80° C.

A filling of a thickness of approximately 200 µm after the printing (wet) and of a thickness of approximately 150 µm after the drying was attained. To completely fill the hole of the film, further filling steps were performed with the cermet paste. 1 to 5 film samples were filled completely with the cermet paste by performing the above filling steps several times.

Laminating the Green Body Films 4 layers of green body film with holes, which are filled as described above, are stacked by means of a metal alignment tool and are isostatically pressed in an oil bath at 70° C. at a pressure of 350 bar for 10 minutes (Laminator-CE-1 by Autoclave Engineers), in order to attain the desired component thickness of 1.6 mm prior to the sintering.

Sintering

The laminate of green body films obtained as above was fired in a high-temperature chamber furnace (FHT-175-10-12 by Arnold Schröder Industriehöfen GmbH), suitable for a maximum temperature of 1750° C. with a chamber size of 200 mm×250 mm×200 mm, in order to sinter the individual layers and cermet fillings. The sintering process took place under atmospheric normal conditions. The temperature was increased from 25 to 450° C. at a rate of 30° C./h. The temperature was then kept constant at 450° C. for 5 h, in order to burn off the organic components in the green body laminate. The temperature was subsequently increased to a maximum temperature in a range of between 1510 and 1560° C. at a rate of 450° C./h and was held constant at this value for a holding time in a range of between 1 and 5 hours. The temperature was then lowered to room temperature at a cooling rate of 450° C./h or at the natural cooling rate, which was slower.

Sintered moulds with a percent by volume of 40% by volume to 45% by volume of platinum in the cermet were obtained.

Post-Treatment

After the firing, the samples were ground and were cut to size to the desired sizes by means of a laser.

The sintered samples were ground to a thickness of 1.0 to 1.1 mm on both sides. Individual areas were separated from the ground samples with the help of a laser cutting method. Areas, which included 5 double rows of cermet conducting elements per sample, were obtained.

Pre-Treatment for the Galvanic Coating

Samples as described above were initially provided with an electrode layer of gold from one side, in order to ensure a sufficient current flow between the direct-current source and the cermet conducting element for the subsequent galvanic coating. To improve the adhesion of the gold layer on the ceramic base body, an intermediate layer of titanium was applied. Both layers were created by means of cathode sputtering. The target layer thicknesses of the titanium layer and of the gold layer were in each case between 1 and 2 µm. The smouldering occurred for 15 minutes at a voltage of 400 V and an argon volume flow of 36 cm$^3$/min with a rotating substrate holder. The sample thereby rested flat on the surface of the substrate holder, in order to coat the sample only on one side. The actual coating by cathode sputtering took place at a base pressure of $5*10^{-5}$ mbar and an argon volume flow of 12 cm$^3$/min.

Galvanic Coating

To create the contact elements on the exposed surfaces of the cermet conducting elements, the samples were contacted via the gold layer applied to the "back side" of the sample. It was avoided thereby that the back side comes into contact with the used gold electrolyte, in order to avoid an unnecessary coating of the electrode layer. To protect the back side against a contact with gold electrolyte, the gold layer was provided as completely as possible with several layers of an adhesive polymer film. The gold layer was subsequently connected to a direct-current source with the help of a metal clamp. The clamp simultaneously served to fasten the sample.

For degreasing, the sample was initially introduced into a solution of 100 g/l of potassium hydroxide with 10 g/l of potassium cyanide, while hanging on the clamp. The sample was connected to a direct-current source (manufacturer: Tandar) as cathode. A platinised titanium expanded metal served as anode. A current density according to an areal current density of 5 A/dm$^2$ was applied. During the cathodic degreasing, a strong gas development was observed at the exposed conductive surfaces of the contact elements. Due to the gas bubbles and the highly alkaline solution, loose particles, adhering fats and other contaminations were removed. It was furthermore observed that the highly alkaline solution removes thin ceramic films from the cermet surfaces.

After the cathodic degreasing, the sample was rinsed a total of three times with distilled water for neutralization purposes and was subsequently introduced into a potassium-gold-cyanide-based gold electrolyte solution (enthrone, Pura Gold 202 B). The sample, in turn, was connected to the direct-current source as cathode. A platinised expanded metal, in turn, served as anode. The sample was moved parallel to the counter electrode (anode) in the electrolyte. In addition, the electrolyte was stirred strongly with the help of a magnetic stirrer and magnetic stirring rods. After the electrolyte solution was heated to 80° C. with the help of a heater, a current density of 5 A/dm$^2$ was applied. After a deposition time of 4 minutes, gold layers with a thickness of 5.3 µm were created on the conducting elements.

The sample was then removed from the electrolyte and was washed intensively under running distilled water. A rinsing was then performed with ethanol and a drying with hot air up to the constant weight.

The obtained contact elements of gold had an average roughness depth Rz of 1.05 µm and a porosity of 0.3%. The contact elements were thus suitable for the attachment of wires with the help of a laser welding method.

FIG. 1 illustrates a schematic cross section of a bushing 100 according to one embodiment. The bushing includes an electrically insulating base body 101. The base body 101 consists of a ceramic, here of aluminum oxide ($Al_2O_3$). The base body 101 has a first surface 103 and a second surface 104. Two conducting elements 102 extend through the base body 101 from the first surface 103 to the second surface 104 of the base body 101. The surfaces 103 and 104 are the flat surfaces or base surfaces of a bushing with the shape of a circular cylinder. The conducting element 102 consists of a cermet. The cermet consists of a ceramic and of a biocompatible metal. The ceramic of the cermet conducting element 102 is aluminum oxide and the metal of the cermet conducting element 102 is platinum. The connection between the conducting element 102 and the base body 101 is co-sintered and thus has a substance-to-substance bond. Within the first surface 103 of the base body 101, the conducting element 102 has a first electrically conductive area 105. Within the second surface 104 of the base body 101, the conducting element 102 further has a second electrically conductive area 106. The first conductive area 105 is covered by a layer-like contact element 107. The second conductive area 106 is further covered by a further layer-like contact element 107. The coverage of the electrically conductive areas 105, 106 by the contact element 107 is substantially without a border thereby. The contact elements 107 consist of gold. The contact elements 107 were obtained by reduction of gold cations to elemental gold with the help of an electrochemical deposition. The contact elements 107 have a porosity of 0.3% and have a sealed porosity.

Figure 2:
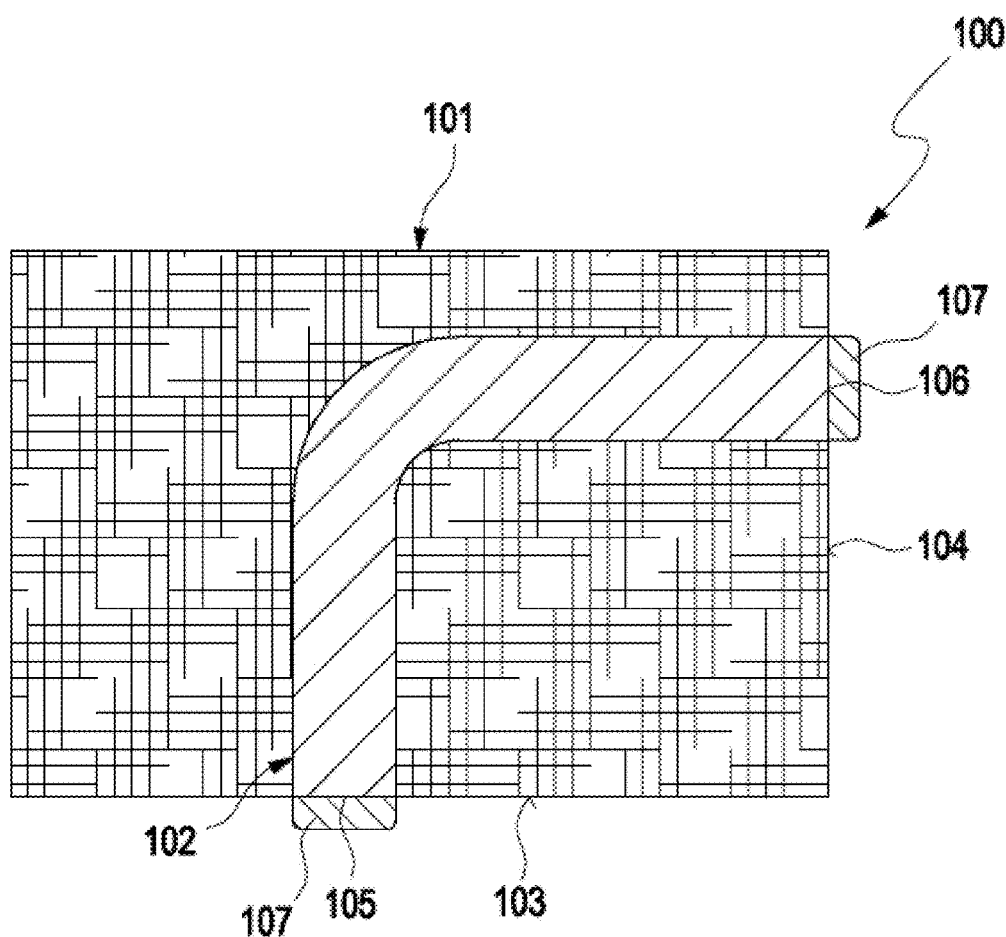
FIG. 2 illustrates a cross sectional illustration of a further embodiment of the bushing according to one embodiment.

FIG. 2 illustrates a schematic cross section of a further embodiment of a bushing 100 according to one embodiment. In this embodiment, the first surface 103 and the second surface 104 of the base body 101 are not located opposite one another, but adjacent to one another across a corner. The first surface 103 is the (curved) jacket surface of a bushing 100 with the basic form of a circular cylinder. The second surface 104 forms a side of the base areas of the circular cylinder. The conducting element 102 extends as wound path from the first surface 103 of the base body 101 to the second surface 104 of the base body 101. The contact element 107 in the curved area of the first surface 103 (jacket surface) covers the conductive area 105 of the conducting element 102 substantially without a border. The contact elements 107 consist of gold. The contact elements 107 were obtained by reduction of gold cations to elemental gold with the help of an electrochemical deposition. The contact elements 107 have a porosity of 0.3%.

Figure 3:
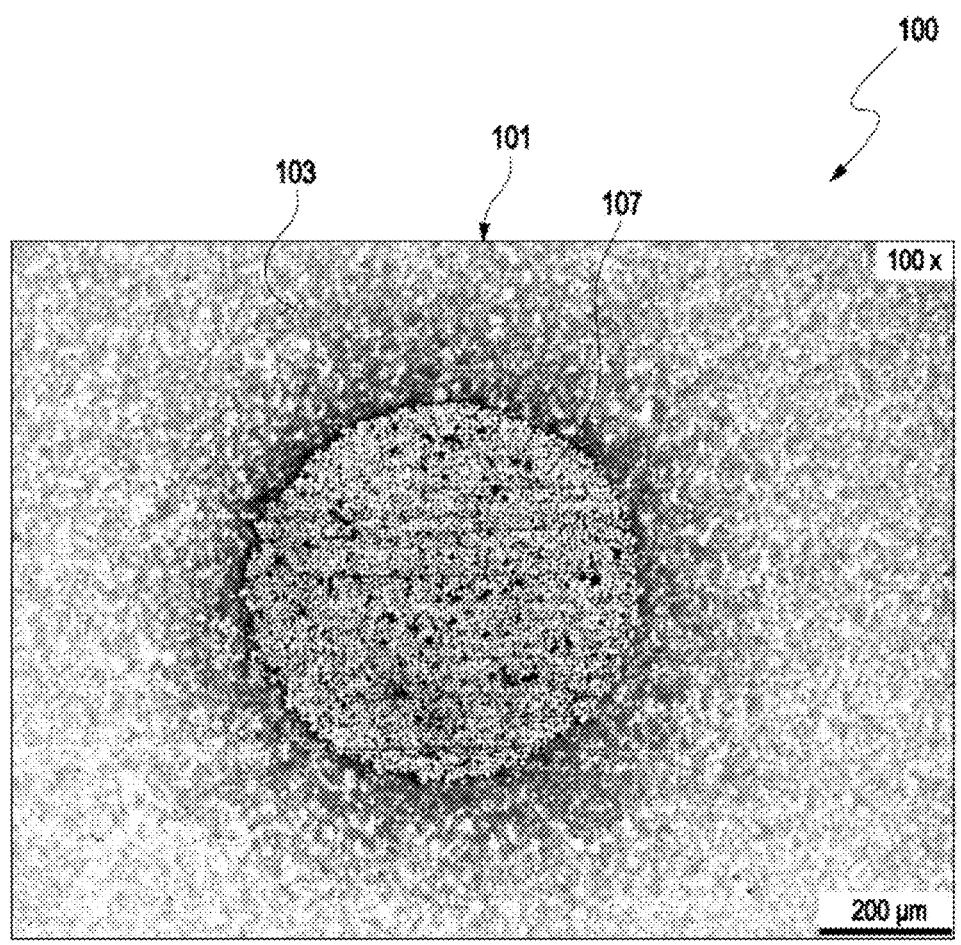
FIG. 3 illustrates an electron-microscopical picture of a top view of a bushing according to one embodiment with contact elements of gold.

FIG. 3 illustrates an electron-microscopic picture (enlargement 50×) of a top view of a section of a bushing 100 according to one embodiment. The first surface 103 of the electrically insulating base body 101 is visible. Four first electrically conductive areas 105 (not visible) of conducting elements 102 (not visible) are located within this surface 103. The electrically conductive areas 105 are covered completely and substantially without a border by the contact elements 107. The surfaces of the contact elements 107 are congruent with the surfaces of the electrically conductive areas 105. The contact elements 107 consist of gold and have a porosity of 0.3%.

Figure 4:
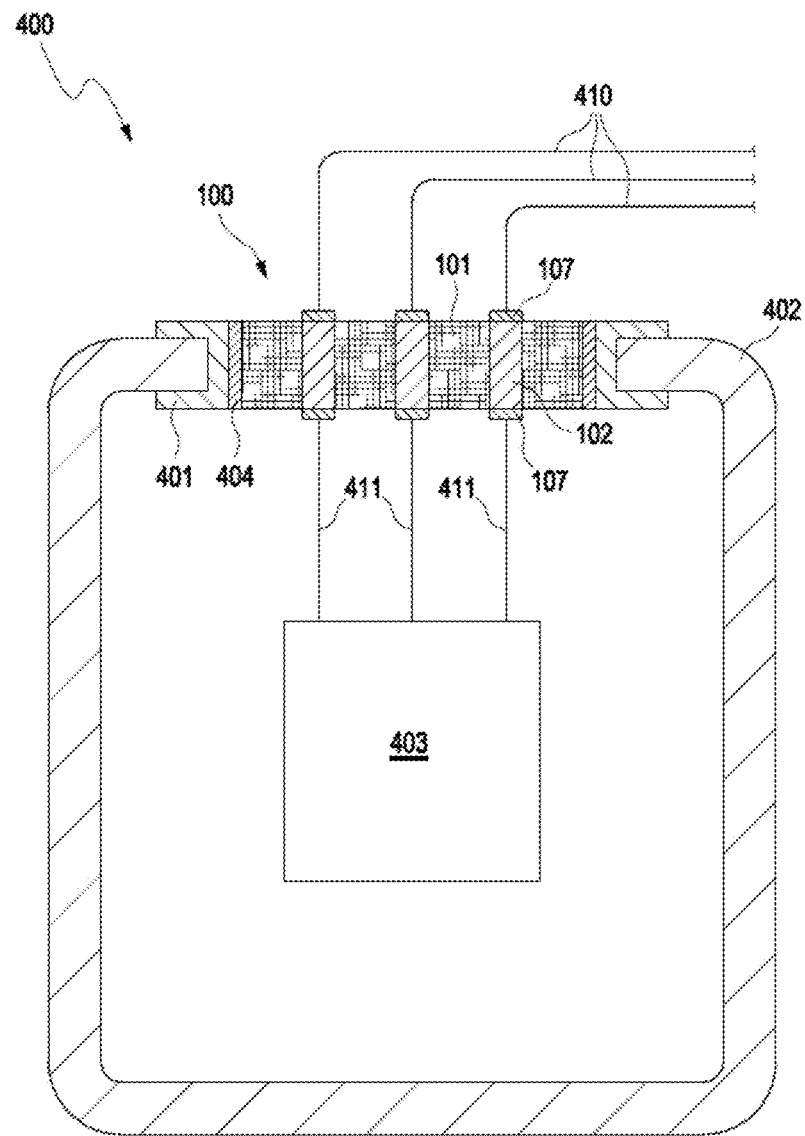
FIG. 4 illustrates an implantable medical device including a bushing according to one embodiment.

FIG. 4 illustrates a schematic cross section of an implantable medical device 400 including an electrical bushing 100 according to one embodiment. The device 400 can be a pacemaker or a defibrillator, for example. The bushing 100 has an electrically insulating base body 101 of aluminum oxide. The base body 101 includes three conducting elements 102. The conducting elements 102 consist of a cermet. The cermet includes aluminum oxide and platinum. The conducting elements 102 are co-sintered with the base body and are thus connected to the base body 101 with a substance-to-substance bond and hermetically. The base body 101 is connected to a flange 401 in a hermetically sealed manner on a peripheral surface. The hermetically sealed connection between base body 101 and flange 401 is realized by means of a solder connection 404. The flange 401, in turn, is connected to a titanium housing 402 of the implantable medical device 400 in a hermetically sealed manner via a welded connection. The implantable medical device 400 includes an interior (housing side) and a bodily fluid side or outer side. A measuring, regulating and control electronics 403 and a battery (not illustrated) is located in the interior of the device 400. The bushing 100 includes three contact elements 107 on the outer side and three contact elements 107 on the inner side of the device. The contact elements 107 on the outer side are in each case connected to metal wires 410. The connection between metal wires 410 and contact elements 107 is a laser welded connection. The metal wires 410 can for example be connected to the IS4 connector of a connecting terminal (not illustrated) of the header block (not illustrated) of the device 400. The contact elements 107 on the inner side are in each case connected to metal wires 411. The connection between metal wires 411 and contact elements 107 is a laser welded connection. The metal wires 411 are connected to the measuring, regulating and control electronics 403 of the implantable device 400.

Figure 5:
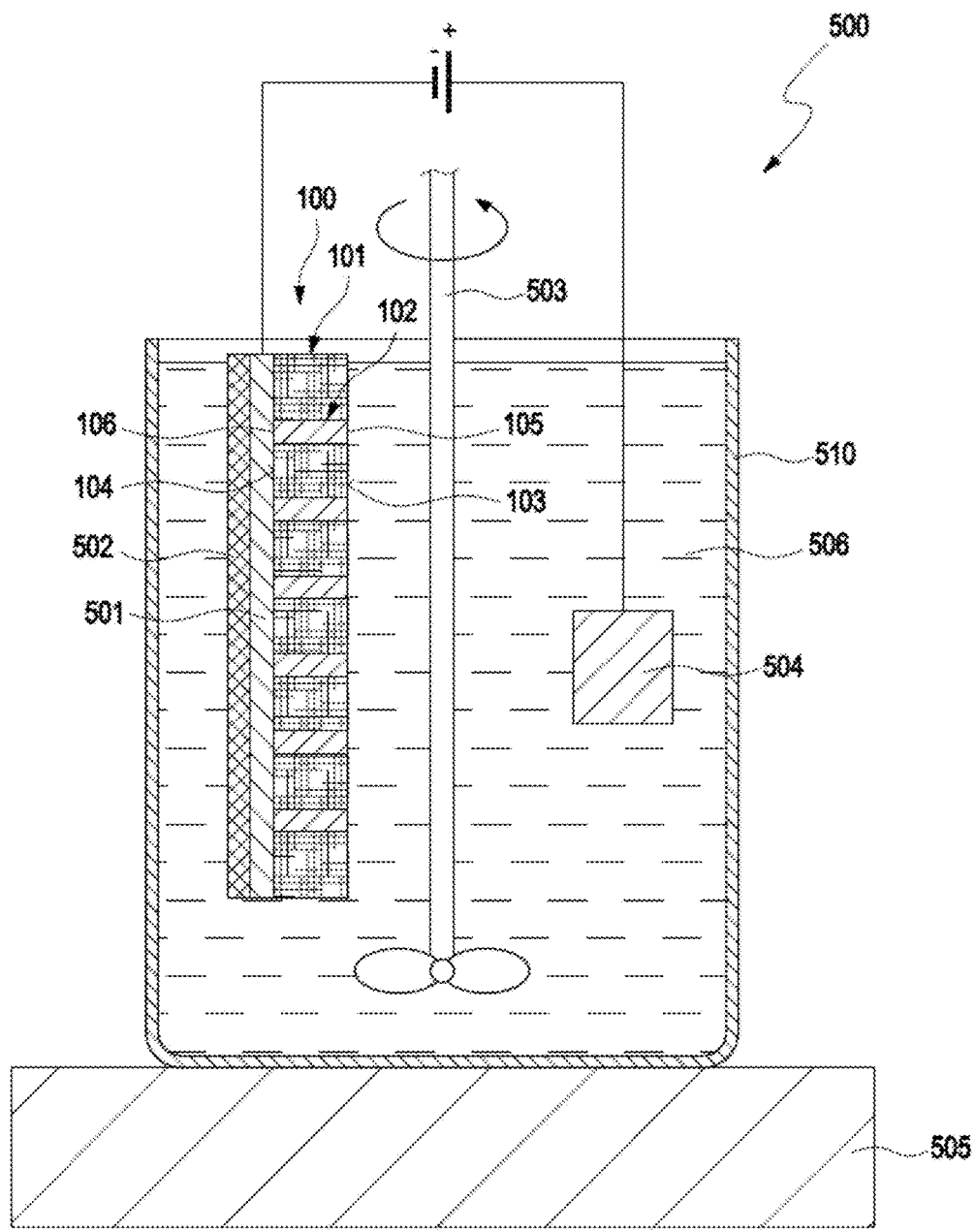
FIG. 5 illustrates a test setup for carrying out the method according to one embodiment.

FIG. 5 illustrates a test setup 500 for carrying out the method according to one embodiment for producing the bushing 100. The test setup 500 is illustrated prior to carrying out the method according to one embodiment. At that point in time, the bushing does not have any contact elements 107. The bushing 100 dips into a receiving vessel 510. The receiving vessel 510 is for example a beaker glass. An electrolyte solution 506 is located in the receiving vessel 510. In the illustrated case, the electrolyte solution 506 is a potassium-gold-cyanide-based gold-electrolyte solution. During the coating of the electrically conductive areas 105 of the bushing 100 with gold, the electrolyte solution 506 is moved with the help of a stirring element 503. The electrolyte solution is simultaneously heated to approx. 80° C. with the help of a heating element 505. The electrical bushing includes an electrode layer 501. The electrode layer 501 can consist of a plurality of layers. In the illustrated case, the electrode layer 501 includes a titanium layer and a gold layer. The titanium layer serves to promote adhesion between the bushing 100 and the gold layer. The electrode layer 501 is superimposed completely by an insulating layer 502. The insulating layer 502 is a flexible polymer layer, which is connected to the electrode layer 501 with the help of an adhesive. The insulating layer 502 prevents the unintentional and unnecessary coating of the electrode layer 501 with gold during the coating process. The electrode layer 501 is connected to a direct-current source (negative pole) with the help of a metal clamp (not illustrated) as cathode. A sufficient current flow to the conductive area 105 of the conducting element 102 is thus ensured. An anode 504, which is also connected to the direct-current source (positive pole), also dips into the electrolyte solution. The anode is a platinized titanium expanded metal. When applying direct current, a gold layer, which serves as contact element 107 for the bushing 100, is formed virtually exclusively on the conductive areas 105 of the bushing 100.

Figure 6:
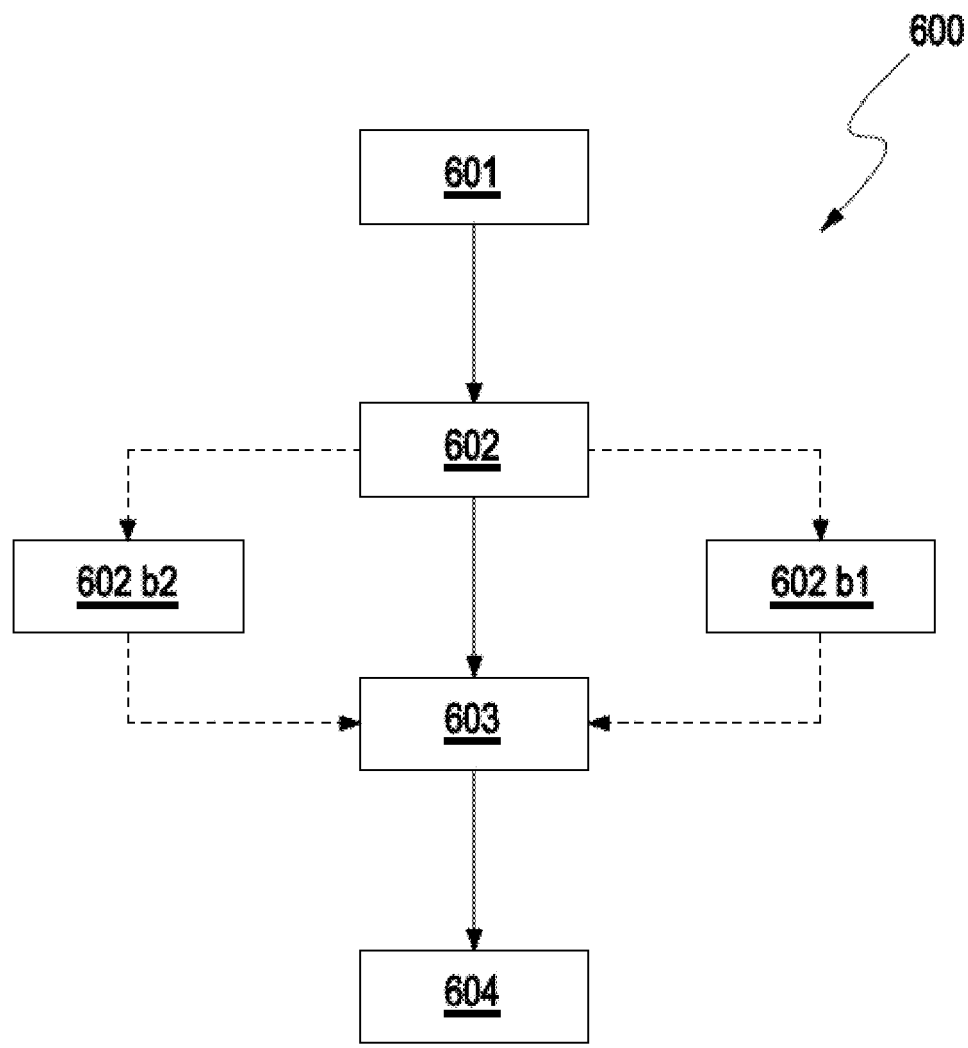
FIG. 6 illustrates a flow chart with method steps of the method according to one embodiment.

FIG. 6 illustrates a flow chart with the method steps of the method 600 according to one embodiment. The method includes the method steps 601 to 604. The method optionally includes the method steps 602 *b*1 and/or 602 *b*2. In method step 601, the electrical bushing 100 is provided without contact elements 107. The electrical bushing 100 includes an electrically insulating base body 101 and at least one electrically insulating conducting element 102. The conducting element 102 includes a cermet. Base body 101 and conducting element 102 are co-sintered. The conducting element 102 extends from a first surface of the base body 103 to a second surface of the base body 104. The conducting element includes a first electrically conductive area 105 within the first surface of the base body 103 and a second electrically conductive area 106 within the second surface of the base body 104. Step 602 includes the application of an electrode layer 501 onto the first surface 103 of the base body 101. The electrode layer 501 includes at least one metal and can consist of a plurality of metal layers. The electrode layer is applied by means of a cathode sputtering process, whereby a titanium layer is initially applied to the first surface of the base body 103 to promote adhesion. A gold layer is subsequently applied to the titanium layer by means of a further cathode sputtering process. In step 602 *b*1, an insulating layer 502 is subsequently optionally applied to the electrode layer 501. The insulating layer 502 includes a polymer and an adhesive, with the help of which the insulating layer 502 is applied to the electrode layer. After the application of the electrode layer 501 according to step 602 or after the application of the insulating layer 502 according to step 602*b*1, a cleaning of the surfaces (step 602 *b*2) of the bushing 100 is optionally carried out by dipping into an alkaline solution and by connecting the electrode layer as a cathode. This cleaning is carried out as a function of the stability of the insulating layer against highly alkaline agents, either after or prior to the application of the insulating layer 501, if an insulating layer is used for the coating process. In the subsequent method step 603, the bushing 100 is introduced into a metal-electrolyte solution 506 and a metallic contact element 107 is formed on the second electroconductive area 106 of the conducting element 102 by means of electrochemical deposition by reduction of metal cations. In the last method step 604, the electrode layer 501 is removed, if applicable together with the insulating layer 502. The removal can take place mechanically by grinding or chemically by means of a location-specific or selective etching. A bushing 100, which is provided with a contact element 107 on one side, is thus obtained. The entire method can optionally be repeated, in order to also provide the first electrically conductive area 105 of the conducting element 102 with a contact element 107. In this case, the electrode layer must not be a firmly adhering metal layer, because the contact element 107 is to remain mechanically undamaged on the second electrically conductive area 106 of the conducting element 102. For this case, a pressed-on copper film is suitable as electrode layer 501.

What is claimed is:

1. An electrical bushing for a medically implantable device comprising:
    an electrically insulating base body and an electrical conducting element, wherein the conducting element includes a cermet, and wherein the base body and the conducting element are connected by a substance-to-substance sintered bond, so that the conducing element is hermetically sealed against the base body;
    the conducting element extending from a first surface of the base body through the base body to a second surface of the base body, wherein the conducting element has a first electrically conductive area within the first surface of the base body and a second electrically conductive area within the second surface of the base body, and at least one of the electrically conductive areas is at least partially superimposed by a layer-like contact element, which includes a metal, so that the conducting element can be connected in an electroconductive manner via the contact element;
    characterized in that the contact element is an electrochemically created layer, and the contact element has a porous structure, wherein the porosity of the contact element is not more than 20%.

2. The electrical bushing of claim 1, wherein the contact element completely superimposes the conductive area.

3. The electrical bushing of claim 1, wherein the amount of the surface of the layer-like contact element is not more than 25% larger than the amount of the surface of the superimposed conductive area.

4. The electrical bushing of claim 1, wherein the contact element has an average layer thickness of between 1 μm and 50 μm.

5. The electrical bushing of claim 1, wherein the contact element has a porosity of 0.1 to 10% by volume.

6. The electrical bushing of claim 1, wherein the contact element has a porosity gradient.

7. The electrical bushing of claim 6, wherein the average porosity of the area adjacent to the conducting element is lowest and that the average porosity increases as the distance from the area adjacent the conducting element increases.

8. The electrical bushing of claim 1, wherein the averaged roughness depth Rz of the layer-like contact element is between 0.2 μm and 20 μm.

9. A method for applying contact elements to electrical bushings comprising:
    a) providing an electrical bushing, wherein the bushing
        i. has an electrically insulating base body and an electrical conducting element, wherein the conducting element includes a cermet,
        ii. the base body and the conducting element are connected by a substance-to-substance sintered connection, so that the conducting element is hermetically sealed against the base body,
        iii. the conducting element extends from a first surface of the base body through the base body to a second surface of the base body,
        iv. the conducting element has a first electrically conductive area within the first surface of the base body and a second electrically conductive area within the second surface of the base body,
    b) applying an electroconductive electrode layer to the first surface of the base body, so that a conductive connection is formed between the first conductive area of the conducting element and the electrode layer,
    c) introducing the bushing into a metal-electrolyte solution and forming a metallic contact element in the second electrically conductive area of the conducting element by means of electrochemical deposition by reducing cations of the metal-electrolyte solution,
    d) removing the electrode layer.

10. The method of claim 9, wherein an insulating layer, which superimposes the electrode layer, is applied in a further step b-1) after b), so that an electrochemical deposition of a metal does not take place in the area of the electrode layer.

11. The method of claim 9, wherein the electrical bushing is immersed into an alkaline solution in a further step b-2) prior to carrying out c), whereby the electrode layer is connected to a direct-current source and is connected as a cathode, in order to clean the surfaces of the electrical bushing.

12. The method of claim 11, wherein the alkaline solution includes sodium hydroxide and/or potassium hydroxide and optionally includes an addition of a cyanide salt.

13. The method of claim 9, wherein the application of the electrically conductive electrode layer in b) takes place by pressing an electrically conductive polymer against the second surface.

14. The method of claim 9, wherein the electrode layer is multi-layered, wherein the multi-layer design includes a conductive paste and a conductive film, which superimposes the conductive paste.

15. The method of claim 9, wherein the current density in response to the electrochemical deposition according to c), based on the surface of the electrically conductive area, is 0.1 to 100 A/dm$^2$.

16. The method of claim 9, wherein the current density in response to the electrochemical deposition according to c), based on the surface of the electrically conductive area, is 0.5 to 30 A/dm2.

17. The method of claim 9, wherein the current density in response to the electrochemical deposition according to c), based on the surface of the electrically conductive area, is 1 to 15 A/dm2.

18. An electrical bushing for a medically implantable device that is obtained by the method of claim 9.

* * * * *